US00PP09767P

United States Patent [19]

Dümmen

[11] Patent Number: Plant 9,767

[45] Date of Patent: Dec. 24, 1996

[54] GERANIUM PLANT NAMED 'HWD RAVELINA'

[75] Inventor: Günter Dümmen, Rheinberg-Eversael, Germany

[73] Assignee: Dummen Jungpflanzenkulturen, Rheinberg-Eversael, Germany

[21] Appl. No.: 521,401

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of Geranium plant named HWD Ravelina, characterized by its single pink and red bicolor flowers; numerous umbels per plant; freely branching plant habit; and dark green leaves.

1 Drawing Sheet

The present invention relates to a new and distinct cultivar of Geranium plant, botanically known as *Pelargonium× hortorum,* known as the variety Duerav, and hereinafter referred to by the cultivar name HWD Ravelina.

The new cultivar is a product of a planned breeding program conducted by the inventor in Rheinberg, Germany. The objective of the breeding program was to develop a new freely-branching single-flowered geranium with pink and red bicolor flowers.

The new cultivar originated from a cross made by the inventor of the nonpatented cultivar Duecon as the male or pollen parent with the patented cultivar Fisrix (U.S. Pat. No. P.P. 7,422) as the female or seed parent.

The cultivar HWD Ravelina was discovered and selected by the inventor as a flowering plant within the progency of the stated cross in a controlled environment in Rheinberg, Germany. Asexual reproduction of the new cultivar by terminal cuttings taken at Rheinberg, Germany, has shown that the unique features of this new Geranium are stabilized and reproduced true to type in successive generations of asexual reproduction.

The following traits have been repeatedly observed and are determined to be the unique characteristics of HWD Ravelina. These characteristics in combination distinguish HWD Ravelina as a new and distinct cultivar:

1. Single pink and red bicolor flowers.
2. Numerous umbels per plant.
3. Freely branching plant habit.
4. Dark green leaves.

In comparison to the parent cultivar Duecon, plants of the new Geranium have single (not semi-double) flowers, bicolor and darker petal color, and darker green foliage color. In comparision to the parent cultivar Fistrix, plants of the new Geranium have larger bright red marks on the petals and plants are much more freely branching.

The accompanying colored photograph illustrates the overall appearance of the new cultivar, showing the colors as true as it is reasonably possible to obtain in colored reproductions of this type. The photograph comprises a top perspective view of a typical potted plant of HWD Ravelina with one plant in a 10-cm container.

The cultivar HWD Ravelina has not been observed under all possible environmental conditions. The phenotype may vary somewhat with variations in environment such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal Geranium.

*Cultivar.*—'HWD Ravelina'.

Parentage:

*Male parent.*—Cultivar Duecon.

*Female parent.*—Patented cultivar Fisrix (U.S. Pat. P.P. No. 7,422).

Propagation:

*Type cutting.*—Terminal cuttings.

*Time to initiate roots.*—Summer: 27° C., 21 days, winter: 20° C., 28 days.

Plant description:

*General appearance.*—Rounded; compact plant size, upright, freely branching.

*Foliage description.*—Arrangement: Generally alternate. Shape: Orbicular with rounded tip and cordate base. Size: Length: 7.5 cm. Width: 8.5 cm. Texture: Velvety; pubescent on upper and under surfaces. Margin: Crenate. Color: Young foliage, upper surface: 147A. Young foliage, under surface: 147B. Mature foliage, upper surface: 147A. Mature foliage, under surface: 147B. Zonation: None. Veins, upper surface: 144A. Veins, under surface: 144A. Petiole: 144A. Venation pattern: Palmate. Petiole: Length: 7 to 11 cm. Diameter: 2 to 3 mm.

*Stem description.*—Internode length: 1 to 1.5 cm. Stem color: 144A. Lateral branch number: 18. Lateral branch length: 7 to 10 cm.

Flowering description:

*Flowering habit.*—Freely flowering. Flowers arranged in umbels.

*Natural flowering season.*—Year-round.

*Flowers borne.*—Flower buds develop in apical leaf axils. Umbels are displayed above the foliage.

*Quantity of inflorescences.*—Very floriferous; usually 11 open umbels and at least 4 developing umbels per plant at one time.

*Umbels.*—Form: Rounded. Diameter: 10 cm. Depth (height): 5 cm.

*Flowers.*—Form: Single. Shape: Rounded. Quantity of flowers per umbel: 18 to 20. Diameter: 4 to 4.5 cm. Depth (height): 2 cm.

*Petals.*—Shape: Obovate with rounded tip. Arrangement: Rosette, overlapping. Quantity: 5. Aspect:

Flat. Size: Length: 2.5 cm. Width: 2.7 cm. Texture: Satiny, smooth. Margin: Entire. Color: When opening, upper surface: 68B with bright red mark, 52A. When opening, under surface: 58A. Upper surface: 68B with bright red mark, 52A. Under surface: 62B. Fading to, upper surface: Base of petals fade to 155D with venous areas, 63B. Fading to, under surface: Base of petals fade to 155D with venous areas, 63B. Diameter of bright red mark: 0.5 to 1.0 cm.

*Petaloids.*—None, single flowers.

*Peduncle* (*umbel stem*).—Angle: Erect, rigid. Length: 12.5 to 15 cm. Pubescence: Very fine. Color: 144A.

*Pedicel* (*individual flower stem*).—Angle: Erect, rigid. Length: 3.3 cm. Pubescence: Very fine. Color: 59A with hint of 144A.

*Flower bud.*—Shape: Ovoid. Length: 1.5 cm. Diameter: 8 mm. Color: 58C/58D.

*Sepals.*—Arrangement: Rosette. Quantity: 5. Size: Length: 1.2 cm. Width: 3 to 5 mm. Shape: Acuminate with apiculate tip. Texture: Velvety. Margin: Entire. Color: Upper surface: 59A at base fading to 144A at tip. Under surface: 59A at base fading to 144A at tip.

*Reproductive organs.*—Androecium: Stamen number: 10 to 11. Anther size: 2 mm. Anther color: 177A to 174D. Anther color: 34C/34D. Gynoecium: Pistil number: 1. Pistil length: 1 cm. Stigma shape: Decurrent. Stigma color: 61C. Style length: 4 mm. Style color: 61C.

*Ploidy level.*—Tetraploid.

Disease resistance: No fungal, bacterial nor viral problems observed.

Seed development: Seed production is very rarely observed.

It is claimed:

1. A new and distinct cultivar of Geranium plant named HWD Ravelina, as illustrated and described.

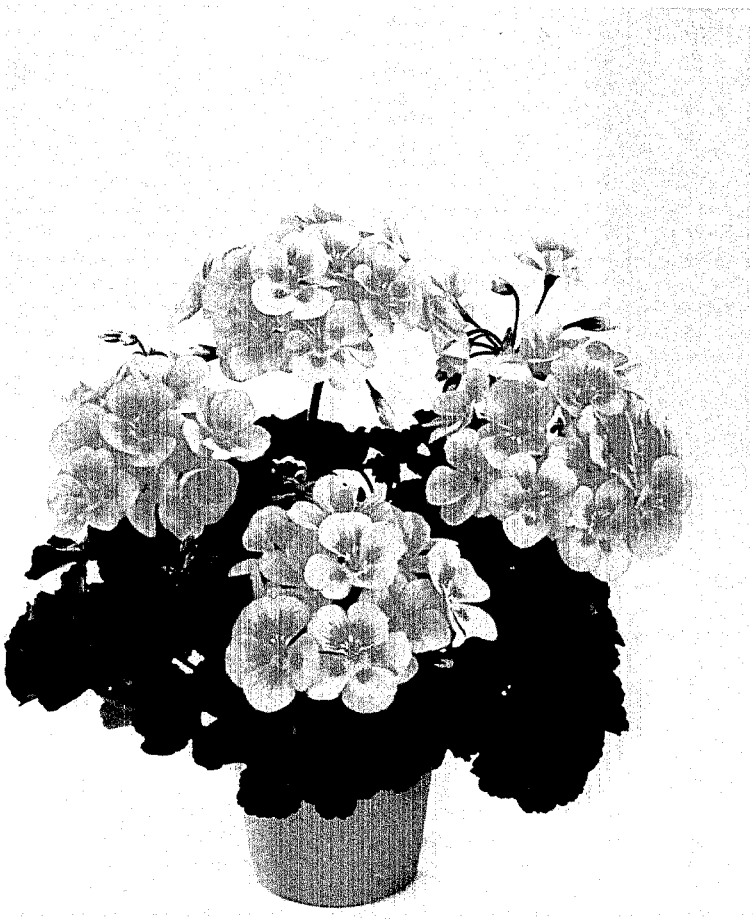

* * * * *